United States Patent [19]

Fobare et al.

[11] Patent Number: 5,136,039

[45] Date of Patent: Aug. 4, 1992

[54] N,N',N'-TRISUBSTITUTED-5-BIS-AMINOMETHYLENE-1,3-DIOXANE-4,6-DIONE INHIBITORS OF ACYL-COA:CHOLESTEROL-ACYL TRANSFERASE

[75] Inventors: William F. Fobare, Hamilton, N.J.; Donald P. Strike, St. Davids, Pa.

[73] Assignee: American Home Products Corporation, New York, N.Y.

[21] Appl. No.: 755,918

[22] Filed: Sep. 6, 1991

[51] Int. Cl.$^5$ .................. A61K 31/47; C07D 277/82
[52] U.S. Cl. ................... 546/163; 546/153; 546/155; 546/160
[58] Field of Search ............... 514/311, 312, 313; 546/153, 155, 156, 157, 163

[56] References Cited

U.S. PATENT DOCUMENTS 4,387,105  6/1983  DeVries et al. .................. 424/322
4,387,106  6/1983  DeVries et al. .................. 424/322

OTHER PUBLICATIONS

DeVries et al., J. Med. Chem., 29, 1131–3 (1986).
Stephen, Monatsche Fur Chemie, 97, p. 45 and pp. 696–702 (1966).
Derwent Abstract 40365k of Japanese J58046084 Sep. 14, 1981.
Augustin et al, Z. Chem. 30, 169–70 (1990).

Primary Examiner—C. Warren Ivy
Assistant Examiner—Catherine Scalzo
Attorney, Agent, or Firm—Richard K. Jackson

[57] ABSTRACT

A compound of the formula:

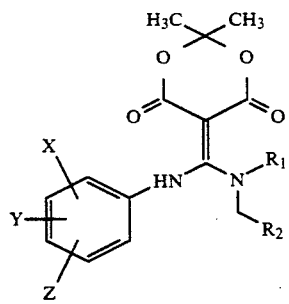

in which X, Y and Z are, independently, hydrogen, halogen, hydroxy, nitro, cyano, carboxyl, trifluoromethyl, phenyl, amino, alkylamino, dialkylamino, alkyl or alkoxy; $R_1$ is alkyl, alkenyl, cycloalkyl, phenyl, benzyl or substituted phenyl or benzyl or alkoxy; $R_2$ is:

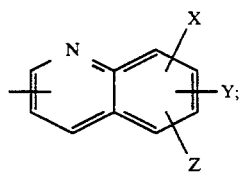

or a pharmaceutically acceptable salt thereof, are ACAT inhibitors.

11 Claims, No Drawings

N,N',N'-TRISUBSTITUTED-5-BIS-AMINOMETHYLENE-1,3-DIOXANE-4,6-DIONE INHIBITORS OF ACYL-COA:CHOLESTEROL-ACYL TRANSFERASE

BACKGROUND OF THE INVENTION

This invention relates to chemical compounds which display inhibition of Acyl-Coenzyme A: Cholesterol Acyltransferase (ACAT). Compounds of this type aid in reducing cholesterol absorption and its effect on atherosclerosis.

Atherosclerosis is the most common form of arteriosclerosis and is characterized by the buildup of phospholipids and esterified cholesterol in large and medium arteries causing them to be inelastic and thus weakened. These inelastic and occluded arteries are the most common cause of ischemic heart disease.

ACAT is an important enzyme for the intracellular esterification of cholesterol. Studies of this enzyme in cultured cells (M.S. Brown, *J. Biol. Chem.* 1980, 617, 458) has shown that increases in ACAT activity represent increases in the presence of cholesterol laden lipoproteins. Regulation of ACAT helps prevent the absorption of cholesterol in the intestinal mucosa, and assists in the reversal of already present atherosclerotic lesions.

DESCRIPTION OF THE INVENTION

In accordance with this invention, there is provided a group of diaminomethylene dioxane dione derivatives of the formula:

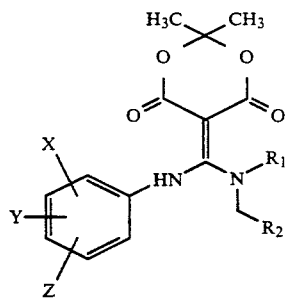

in which
X, Y and Z are, independently, hydrogen, halogen, hydroxy, nitro, cyano, carboxyl, trifluoromethyl, phenyl, amino, alkylamino of 1 to 6 carbon atoms, dialkylamino in which each alkyl group has 1 to 6 carbon atoms, alkyl of 1 to 12 carbon atoms or alkoxy of 1 to 12 carbon atoms;

$R_1$ is alkyl of 1 to 18 carbon atoms, alkenyl of 1 to 18 carbon atoms, cycloalkyl of 5 to 8 carbon atoms, phenyl, benzyl or substituted phenyl or benzyl where the substituents are alkyl of 1 to 12 carbon atoms or alkoxy of 1 to 12 carbon atoms;

$R_2$ is

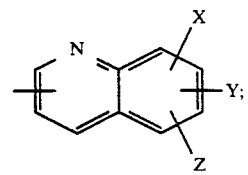

or a pharmaceutically acceptable salt thereof.

The halogen substituent referred to above may be chlorine, bromine, fluorine or iodine, fluorine being preferred. The pharmaceutically acceptable salts are derived from known inorganic or organic acids such as hydrochloric, hydrobromic, sulfuric, nitric, phosphoric, methanesulfonic, ethanesulfonic, hydroxyethanesulfonic, toluene sulfonic, naphthalenesulfonic, formic, acetic, propionic, oxalic, succinic, glycollic, lactic, malic, tartaric, citric, ascorbic, maleic, hydroxymaleic, pyruvic, phenylacetic, benzoic, paraamino benzoic, para-hydroxybenzoic, salicylic, sulfanilic acids, and the like.

Of these compounds, those preferred on the basis of their in vitro and in vivo potency are:

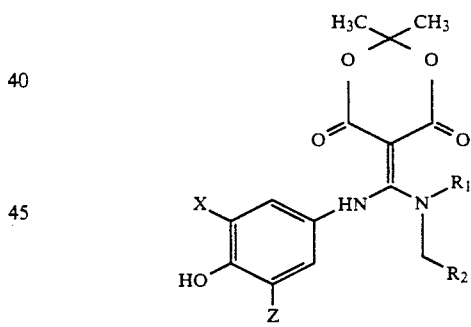

in which
X and Z are, independently, alpha branched alkyl of 1 to 6 carbon atoms;

$R_1$ is alkyl of 1 to 18 carbon atoms; and
$R_2$ is 2-, 3- or 4-quinolinyl;

or a pharmaceutically acceptable salt thereof.

The compounds of this invention are prepared by conversion of 2,2-dimethyl-1,3-dioxane-4,6-dione to the corresponding 5-bis-(methylthio) methylene derivative with carbon disulfide and methyl iodide in dimethylsulfoxide in the presence of a base such as triethylamine, followed by sequential displacement of the methylthio groups with the desired amines, thusly:

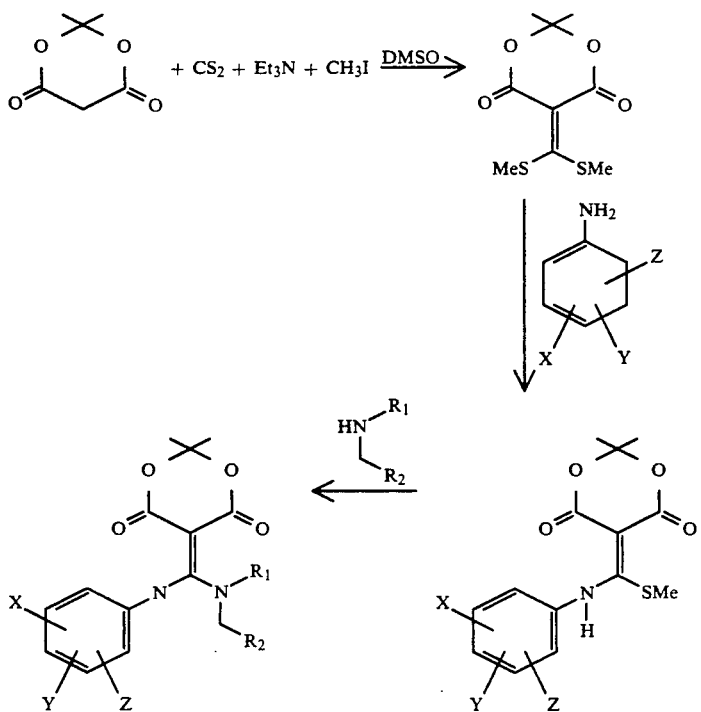

The following examples illustrate without limitation the preparation of representative compounds of this invention.

METHOD A

EXAMPLE 1

5-[[[3,5-Bis(1,1-dimethylethyl)-4-hydroxyphenyl-]amino][hexyl(4-quinolinylmethyl)amino]methylene]-2,2-dimethyl-1,3-dioxane-4,6-dione

Procedure 1

To a solution of 6.4 g (25.8 mmol) of 5-[bis(methylthio)methylene]-2,2-dimethyl-1,3-dioxane-4,6-dione and 4.84 g (56.0 mmol) of sodium bicarbonate in 10 mL of degassed DMSO was added 10.0 g (36.0 mmol) of 3,5-di-t-butyl-4-hydroxyaniline hydrochloride in 30 mL of degassed DMSO over a 5 hour period at room temperature. Stirring was continued for an additional 19 hours. The reaction mixture was poured into cold $H_2O$ and the product filtered. The solid was dried and dissolved in ethyl acetate and filtered again. The solvent was removed at reduced pressure and the residue submitted to a column chromatography on silica gel (3:1 to 2:1 hexane-ethyl acetate) to yield 9.8 g (90%) of a solid that was used without further purification.

Procedure 2

To a solution of 3.05 mL (98.8 mmol) of hexylamine and 16.5 mL (33 mmol) of 2N HCl in 25 mL of methanol was dissolved 2.59 g (16.5 mmol) of 4-quinolinecarboxaldehyde. To this mixture was added 0.62 g (9.9 mmol) of sodium cyanoborohydride. After 1 hour the pH was lowered to 7.8 with 2N HCl. This stirred at room temperature for 1 hour. The solvents were removed at reduced pressure and the residue was added to 30 mL of $H_2O$ and the solution was acidified to pH2 with concentrated HCl. This solution was washed 3×50 mL of diethyl ether and then it was made basic with NaOH to pH12. The aqueous solution was extracted 3 times with 50 mL of $CHCl_3$ which extracts were combined, dried ($Na_2SO_4$) and the solvent removed at reduced pressure. Column chromatography of the residue on silica gel (90:10 ethyl acetate - hexane to 5:95 triethylamine-ethyl acetate) yielded 2.5 g (64%) of an oil which was used without further purification.

Procedure 3

To a solution of 1.2 g (2.86 mmol) of the compound from Method A, procedure 1 in 30 mL of acetonitrile was added 0.73 g (3.0 mmol) of the amine from Method A, procedure 2, 0.4 mL (2.86 mmol) of triethylamine and 0.47 g (1.57 mmol) of mercuric sulfate. The mixture was allowed to stir at reflux for 4 hours. The solution was cooled, diluted with ethyl acetate and filtered through celite. The solvents were removed at reduced pressure and column chromatography of the residue on silica gel (80:20 ethyl acetate - hexanes to 100% ethyl acetate) yielded 0.52 g (46%) of a yellow powder. This was recrystallized from ethyl acetate - hexanes to yield the title compound as a yellow solid (mp 127°–133° C.). IR (KBr): 3420, 3222, 2950, 2868, 1612 1565, 1507, 1462, 1429, 1381, 1360, 1251, 1229, 1198, 1161, 1113, 1089, 1021, 922, 883, 782 and 762 $cm^{-1}$. $^1H$ NMR (400 MHz, $CDCl_3$): δ9.60 (br s, 1H), 8.90 (d, 1H, J=4.48 Hz), 8.16 (d, 1H, J=8.36), 7.74–7.61 (m, 3H), 7.55 (t, 1H, J=7.28 Hz), 6.71 (s, 2H), 5.22 (s, 1H), 4.90 (s, 2H), 3.23 (br s, 2H), 1.67 (br s, 8H), 1.22 (br s, 24H), 0.83 (t, 3H, J=6.76 Hz).

Elemental analysis for $C_{37}H_{49}N_3O_5$: Calc'd: C, 72.17; H, 8.02; N, 6.82. Found: C, 71.78; H, 8.00; N, 6.60.

METHOD B

EXAMPLE 2

5-[[(2,4-Dimethoxyphenyl)amino][hexyl(4-quinolinylmethyl)amino]methylene]-2,2-dimethyl-1,3-dioxane-4,6-dione

Procedure 1

To a solution containing 2.0 g (8.05 mmol) of 5-[bis(methylthio)methylene]-2,2-dimethyl-1,3-dioxane-4,6-dione 1 in 40 mL of t-butanol, was added 1.23 g (8.05 mmol) of 2,4-dimethoxyaniline. The reaction mixture was allowed to stir at reflux for 24 hours. The mixture was cooled to room temperature and diluted with hexanes. The solid was filtered and used without further purification. Isolated: 2.3 g, 81% yield.

Procedure 2

To a solution of 0.84 g (2.38 mmol) of the product from Method B, procedure 1, was added 30 mL of acetonitrile, 0.33 g (1.31 mmol) of mercuric sulfate, 0.33 mL (2.38 mmol) of triethylamine and 0.64 g (2.6 mmol) of the amine synthesized in Method A, procedure 2. The reaction mixture was allowed to stir at reflux for 1.5 hours. The mixture was then cooled to room temperature, diluted with ethyl acetate and filtered through celite. The solvent was removed at reduced pressure and column chromatography of the residue on silica gel (ethyl acetate to 90:10 ethyl acetate-ethanol) yielded a solid which after recrystallization from diisopropyl ether yielded 1.08 g (83%) of the title compound as a white solid (mp 144°-147° C.). IR (KBr): 3420, 2930, 2855, 1700, 1633, 1571, 1517, 1464, 1386, 1352, 1312, 1204, 1160, 1088, 1031 and 930 cm$^{-1}$. $^1$H NMR (400 MHz, CDCl$_3$): δ8.90 (d, 1H, J=4.36 Hz), 8.8 (br s, 1H exchangeable), 8.17 (d, 1H, J=8.08 Hz), 7.76-7.66 (m, 3H), 7.54 (t, 1H, J=7.28 Hz), 6.91 (d, 1H, J=8.52 Hz), 6.33 (d, 1H, J=2.48 Hz), 6.26 (dd, 1H, J=8.52, 2.52 Hz), 4.94 (br s, 2H), 3.75 (s, 3H), 3.58 (s, 3H), 3.26 (br s, 2H), 1.61 (br s, 8H), 1.25 (br s, 6H), 0.83 (t, 3H, J=6.84 Hz).

Elemental analysis for C$_{31}$H$_{37}$N$_3$O$_6$: Calc'd: C, 67.99; H, 6.81. Found: C, 67.84; H, 6.91.

EXAMPLE 3

5-[[[3,5-Bis(1,1-dimethylethyl)-4-hydroxyphenyl]amino][hexyl(2-quinolinylmethyl)amino]methylene]-2,2-dimethyl-1,3-dioxane-4,6-dione This compound was synthesized using the methodology described in Method A except 2-quinolinecarboxaldehyde was substituted for 4-quinolinecarboxaldehyde to yield the title compound as a white solid (mp 161°-163° C.).

Elemental analysis for C$_{37}$H$_{49}$N$_3$O$_5$: Calc'd: C, 72.17; H, 8.02. Found: C, 71.91; H, 8.09.

EXAMPLE 4

5-[[(2,4-Dimethoxyphenyl)amino][hexyl(2-quinolinylmethyl)amino]methylene]-2,2-dimethyl-1,3-dioxane-4,6-dione This compound was synthesized using the methodology described in Method B except 2-quinolinecarboxaldehyde was substituted for 4-quinolinecarboxaldehyde to yield the title compound as a light brown solid (mp 106°-109° C.).

Elemental analysis for C$_{31}$H$_{37}$N$_3$O$_6$: Calc'd: C, 67.99; H, 6.81. Found: C, 67.54; H, 6.82.

EXAMPLE 5

5-[[(2,4-Dimethoxyphenyl)amino]-[1-methylhexyl)(2-quinolinylmethyl)amino]methylene]-2,2-dimethyl-1,3-dioxane-4,6-dione This compound was synthesized using the methodology described in Method A except 2-aminoheptane was used in place of hexylamine and 2-quinolinecarboxaldehyde was used instead of 4-quinolinecarboxaldehyde to yield the title compound as a solid (mp 148°-151° C.).

Elemental analysis for C$_{32}$H$_{39}$N$_5$O$_6$: Calc'd: C, 58.43; H, 7.00; N, 7.48. Found: C, 58.10; H, 7.13; N, 7.29.

EXAMPLE 6

5-[[[3,5-Bis(1,1-dimethylethyl)-4-hydroxyphenyl]amino][1-methylhexyl)(2-quinolinylmethyl)amino]methylene]-2,2-dimethyl-1,3-dioxane-4,6-dione This compound was synthesized using the methodology described in Method A except 2-aminoheptane was used in place of hexylamine and 2-quinolinecarboxaldehyde was used instead of 4-quinolinecarboxaldehyde to yield the title compound as a solid (mp 124°-128° C.).

Elemental analysis for C$_{38}$H$_{51}$N$_3$O$_5$: Calc'd: C, 72.47; H, 8.16; N, 6.67. Found: C, 72.16; H, 8.04; N, 6.29.

EXAMPLE 7

5-[[(2,4-Dimethoxyphenyl)amino][(1-methylhexyl)(4-quinolinylmethyl)amino]methylene]-2,2-dimethyl-1,3-dioxane-4,6-dione This compound was synthesized using the same methodology described in Method B except that 2-aminoheptane was substituted for hexylamine to yield the title compound as a solid (mp 197°-202° C.).

Elemental analysis for C$_{32}$H$_{39}$N$_3$O$_6$: Calc'd: C, 68.43; H, 7.00; N, 7.48. Found: C, 68.41; H, 6.89; N, 7.48.

EXAMPLE 8

4-[[[3,5-Bis(1,1-dimethylethyl)-4-hydroxyphenyl]amino][(1-methylhexyl)(4-quinolinylmethyl)amino]methylene]-2,2-dimethyl-1,3-dioxane-4,6-dione This compound was synthesized using the same methodology described in Method A except that 2-aminoheptane was substituted for methylamine to yield the title compound as a solid (mp 147°-151° C.).

Elemental analysis for C$_{38}$H$_{51}$N$_3$O$_5$: Calc'd: C, 72.46; H, 8.16; N, 6.67. Found: C, 72.11; H, 8.21; N, 6.35.

EXAMPLE 9

5-[[[3,5-Bis(1,1-dimethylethyl)-4-hydroxyphenyl]amino][hexyl(3-quinolinylmethyl)amino]methylene-2,2-dimethyl-1,3-dioxane-4,6-dione This compound was synthesized using the methodology described in Method A except 3-quinolinecarboxaldehyde was substituted for 4-quinolinecarboxaldehyde to yield a light orange powder (mp 130°-136° C.).

Elemental analysis for C$_{37}$H$_{49}$N$_3$O$_5$: Calc'd: C, 72.17; H, 8.02; N, 6.82. Found: C, 71.74; H, 8.07; N, 6.81.

The ability of the compounds of this invention to inhibit acyl-coenzyme A: cholesterol acyltransferase was established by initially showing that they inhibited intracellular cholesterol esterification by subjecting them to the standard experimental test procedure of Ross et al., J. Biol. Chem. 259 815 (1984). The results of these studies are presented in:

TABLE I

| Example | % Inhib. (Concentration - μM) | IC$_{50}$ (μM) |
|---|---|---|
| 1 | 69 (25) | 2.96 |
| 3 | 55 (25) | 2.33 |
| 4 | 72 (25) | 5.16 |
| 5 | 90 (25) | 2.42 |
| 6 | 95 (25) | 1.55 |
| 7 | 51 (25) | 9.41 |
| 8 | 97 (25) | 1.65 |
| 9 | 98 (25) | 1.35 |

Representative compounds were further tested in vivo to establish the percent inhibition of cholesterol absorption. In this study, normal rats were dosed (oral gavage) with $^{14}$C-cholesterol plus the test compound. Blood samples taken exactly six hours later were analyzed and the percent inhibition of cholesterol absorption was calculated as shown in:

TABLE II

In Vivo Testing $^{14}$C-Cholesterol Absorption in Normal Rats

| Example | Dose mg/kg | % Inhibition of Absorption |
|---|---|---|
| 1 | 10 | −72 |
| 2 | 3 | −2 |
| 3 | 3 | −11 |

In addition, the product of Example 1 was studied in vivo in the cholesterol-cholic acid fed rat to determine the percent decrease of cholesterol in their plasma. This study involves rats which are, prior to testing, trained for one week to eat over a four hour time period each day. Upon initiation of the experiment, the rats diet is supplemented with 1.0 percent cholesterol and 0.25 percent cholic acid. The rats are dosed with the test compound by oral gavage just prior to and just following the four hour feeding period. This is repeated for four days. On the fifth day, the rats are sacrificed and the total plasma cholesterol content is determined. The percent decrease in elevated plasma cholesterol levels is calculated in comparison with normal-fed controls. The compound of Example 1 at 10 mg/kg resulted in a 50 percent decrease in plasma cholesterol.

From these data, the ability of the compounds to inhibit ACAT is clearly established. Hence, the compounds of this invention are useful in the treatment of those disease states which are amenable to treatment by reduction of the rate of cholesterol esterification, the rate of accumulation and deposits of cholesteryl esters on arterial walls and the rate of formation of atheromatous lesions. As such, the antiatherosclerotic agents of this invention may be administered to a mammal in need of intracellular cholesteryl ester concentration reduction orally or parenterally in an amount sufficient to inhibit ACAT catalysis of cholesterol esterification.

The compounds of this invention may be administered by themselves or in combination with pharmaceutically acceptable liquid or solid carriers. Oral administration in conventional formulations as tablets, capsules, powders, or suspensions is preferred.

A solid carrier can include one or more substances which may also act as flavoring agents, lubricants, solubilisers, suspending agents, fillers, glidants, compression aids, binders or tablet-disintegrating agents; it can also be an encapsulating material. In powders, the carrier is a finely divided solid which is in admixture with the finely divided active ingredient. In tablets, the active ingredient is mixed with a carrier having the necessary compression properties in suitable proportions and compacted in the shape and size desired. The powders and tablets preferably contain up to 99% of the active ingredient. Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

Liquid carriers are used in preparing solutions, suspensions, emulsions, syrups, elixirs and pressurized compositions. The active ingredient can be dissolved or suspended in a pharmaceutically acceptable liquid carrier such as water, an organic solvent, a mixture of both of pharmaceutically acceptable oils or fats. The liquid carrier can contain other suitable pharmaceutical additives such as solubilisers, emulsifiers, buffers, preservatives, sweeteners, flavoring agents, suspending agents, thickening agents, colors, viscosity regulators, stabilisers or osmo-regulators. Suitable examples of liquid carriers for oral and parenteral administration include water (particularly containing additives as above, e.g. cellulose derivatives, preferably sodium carboxymethyl cellulose solution), alcohols (including monohydric alcohols and polyhydric alcohols, e.g., glycols) and their derivatives, and oils (e.g. fractionated coconut oil and arachis oil). For parenteral administration, the carrier can also be an oil ester such as ethyl oleate and isopropyl myristate. Sterile liquid carriers are used in sterile liquid form compositions for parenteral administration. The liquid carrier for pressurized compositions can be halogenated hydrocarbon or other pharmaceutically acceptable propellent.

Liquid pharmaceutical compositions which are sterile solutions or suspensions can be utilized by, for example, intramuscular intraperitoneal or subcutaneous injection. Sterile solutions can also be administered intravenously. When the compound is orally active, it can be administered orally either in liquid or solid composition form.

Preferably, the pharmaceutical composition is in unit dosage form, e.g. as tablets or capsules. In such form, the composition is sub-divided in unit dose containing appropriate quantities of the active ingredient; the unit dosage forms can be packaged compositions, for example, packeted powders, vials, ampoules, prefilled syringes or sachets containing liquids. The unit dosage form can be, for example, a capsule or tablet itself, or it can be the appropriate number of any such compositions in package form.

The dosage to be used in the treatment of a specific hypercholesterolemic/atherosclerotic condition must be subjectively determined by the attending physician. The variables involved include the extent of the disease state, size, age and response pattern of the patient.

What is claimed is:

1. A compound of the formula:

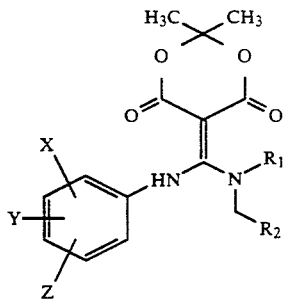

in which

X, Y and Z are, independently, hydrogen, halogen, hydroxy, nitro, cyano, carboxyl, trifluoromethyl, phenyl, amino, alkylamino of 1 to 6 carbon atoms, dialkylamino in which each alkyl group has 1 to 6 carbon atoms, alkyl of 1 to 12 carbon atoms or alkoxy of 1 to 12 carbon atoms;

$R_1$ is alkyl of 1 to 18 carbon atoms, alkenyl of 1 to 18 carbon atoms, cycloalkyl of 5 to 8 carbon atoms, phenyl, benzyl or substituted phenyl or benzyl where the substituents are alkyl of 1 to 12 carbon atoms or alkoxy of 1 to 12 carbon atoms;

$R_2$ is

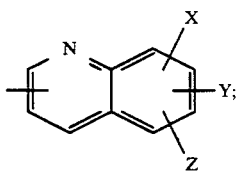

or a pharmaceutically acceptable salt thereof.

2. A compound of claim 1 of the formula:

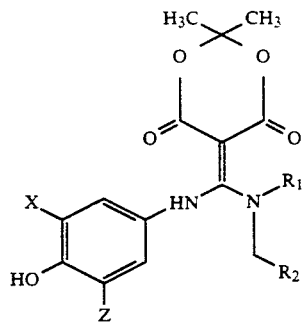

in which
X and Z are, independently, alpha branched alkyl of 1 to 6 carbon atoms;
$R_1$ is alkyl of 1 to 18 carbon atoms; and
$r_2$ is 2-, 3- or 4-quinolinyl;
or a pharmaceutically acceptable salt thereof.

3. A compound of claim 1 which is 5-[[[3,5-bis(1,1-dimethylethyl)-4-hydroxyphenyl]amino[hexyl(4-quinolinylmethyl)amino]methylene]-2,2-dimethyl-1,3-dioxane-4,6-dione, or a pharmaceutically acceptable salt thereof.

4. A compound of claim 1 which is 5-[[(2,4-dimethoxyphenyl)amino][hexyl(4-quinolinylmethyl)amino]methylene]-2,2-dimethyl-1,3-dioxane-4,6-dione, or a pharmaceutically acceptable salt thereof.

5. A compound of claim 1 which is 5-[[[3,5-bis(1,1-dimethylethyl)-4-hydroxyphenyl]amino][hexyl(2-quinolinylmethyl)amino]methylene]-2,2-dimethyl-1,3-dioxane-4,6-dione, or a pharmaceutically acceptable salt thereof.

6. A compound of claim 1 which is 5-[[(2,4-dimethoxyphenyl)amino][hexyl(2-quinolinylmethyl)amino]methylene]-2,2-dimethyl-1,3-dioxane-4,6-dione, or a pharmaceutically acceptable salt thereof.

7. A compound of claim 1 which is 5-[[(2,4-dimethoxyphenyl)amino]-[1-methylhexyl)(2-quinolinylmethyl)amino]methylene]-2,2-dimethyl-1,3-dioxane-4,6-dione, or a pharmaceutically acceptable salt thereof.

8. A compound of claim 1 which is 5-[[[3,5-bis(1,1-dimethylethyl)-4-hydroxyphenyl]amino][1-methylhexyl)(2-quinolinylmethyl)amino]methylene]-2,2-dimethyl-1,3-dioxane-4,6-dione, or a pharmaceutically acceptable salt thereof.

9. A compound of claim 1 which is 5-[[(2,4-dimethoxyphenyl)amino][(1-methylhexyl)(4-quinolinylmethyl)amino]methylene]-2,2-dimethyl-1,3-dioxane-4,6-dione, or a pharmaceutically acceptable salt thereof.

10. A compound of claim 1 which is 4-[[[3,5-bis(1,1-dimethylethyl)-4-hydroxyphenyl]amino][(1-methylhexyl)(4-quinolinylmethyl)amino]methylene]-2,2-dimethyl-1,3-dioxane-4,6-dione, or a pharmaceutically acceptable salt thereof.

11. A compound of claim 1 which is 5-[[[3,5-bis(1,1-dimethylethyl)-4-hydroxyphenyl]amino][hexyl(3-quinolinylmethyl)amino]methylene-2,2-dimethyl-1,3-dioxane-4,6-dione, or a pharmaceutically acceptable salt thereof.

* * * * *